United States Patent
Hansen

(12) 
(10) Patent No.: US 8,531,671 B1
(45) Date of Patent: Sep. 10, 2013

(54) APPARATUS AND METHODS FOR DETERMINING THE CONCENTRATION OF BLACK CARBON PARTICLES IN A COMBUSTION EXHAUST

(75) Inventor: Anthony D. A. Hansen, Berkeley, CA (US)

(73) Assignee: Magee Scientific Corporation, Berkely, CA (US)

(*) Notice: Subject to any disclaimer, the term of this patent is extended or adjusted under 35 U.S.C. 154(b) by 378 days.

(21) Appl. No.: 12/960,344

(22) Filed: Dec. 3, 2010

Related U.S. Application Data

(60) Provisional application No. 61/267,042, filed on Dec. 5, 2009, provisional application No. 61/322,060, filed on Apr. 8, 2010.

(51) Int. Cl.
*G01N 21/00* (2006.01)
*G01N 1/00* (2006.01)
*G01N 33/28* (2006.01)

(52) U.S. Cl.
USPC .............. 356/438; 356/38; 356/432; 356/436

(58) Field of Classification Search
None
See application file for complete search history.

(56) References Cited

U.S. PATENT DOCUMENTS

| 4,893,934 | A | 1/1990 | Hansen | |
|---|---|---|---|---|
| 6,205,842 | B1 * | 3/2001 | Patashnick et al. | .......... 73/28.01 |
| 6,422,060 | B1 * | 7/2002 | Patashnick et al. | .......... 73/28.01 |
| 2004/0156036 | A1 | 8/2004 | Petzold et al. | |

OTHER PUBLICATIONS

Batelle; Environmental Technology Verification Report, "Magee Scientific Aethalometer Particulate Carbon Monitor"; Aug. 2001.
"The Aethalometer—An Instrument for Real-Time Measurement of Optical Absorption by Aerosol Particles", Hansen, A. D. A., Rosen, H. and Novakov, T., *The Science of the Total Environment* 36 (1984), pp. 191-196.

* cited by examiner

*Primary Examiner* — Gordon Stock, Jr.
(74) *Attorney, Agent, or Firm* — Steven R. Vosen

(57) ABSTRACT

Apparatus and methods are described for determining particulate concentrations in an exhaust gas. One embodiment provides a method of analyzing particles in a gas using an apparatus including a probe and an analyzer. The method includes obtaining a sample of particle laden gas through the probe; obtaining ambient air through the probe; diluting the sample with the ambient air; and providing the diluted sample to the analyzer. Another embodiment provides an apparatus for analyzing particles in a gas. The apparatus includes a probe adapted to accept a gas or ambient air; a volume to dilute the gas with the ambient air; an analyzer responsive to particles in the gas; and electronics to operate the apparatus. The electronics instructs a user to first provide a sample and then provide ambient air into the volume, and then analyzes substantially all of the sample and ambient air for particles.

27 Claims, 3 Drawing Sheets

APPARATUS AND METHODS FOR DETERMINING THE CONCENTRATION OF BLACK CARBON PARTICLES IN A COMBUSTION EXHAUST

CROSS-REFERENCE TO RELATED APPLICATIONS

This application claims the benefit of U.S. Provisional Application No. 61/267,042, filed Dec. 5, 2009 and U.S. Provisional Application No. 61/322,060, filed Apr. 8, 2010, the entire contents of which hereby incorporated by reference herein and made part of this specification.

BACKGROUND OF THE INVENTION

1. Field of the Invention

The present invention generally relates to apparatus and methods for measuring pollutants in an exhaust and more particularly to an apparatus and method to determine the concentration of particles in a combustion exhaust stream.

2. Discussion of the Background

Combustion processes generally produce gaseous and particulate species as by-products. In particular, the combustion of carbon-containing fuels such as petroleum products; bio-derived liquid fuels; coal; and biomass such as wood, may create carbonaceous particles. These particles may include "black carbon" (or BC), which is implicated in local, regional and global climate change, due to their ability to absorb sunlight and change the properties of clouds; and which are also well-known tracers for adverse human health impacts arising from their inhalation and deposition in the lungs and body tissues.

The emission of black carbon particles is highly variable from one source to another, and can not be predicted: the emissions must be measured. Black carbon particulate emission is found to depend strongly on the type of fuel; the quality of combustion; and, for internal combustion engine sources, the degree of maintenance of the engine. The ability to make a rapid and accurate measurement of the concentration of black carbon in an exhaust stream is therefore highly advantageous for determining a source's emissions strength if required to assess potential health risk; and for examining the emissions from a suite or set of sources such as a fleet of vehicles to permit determination of compliance with an emissions standard, or as a means of determining which engines require remedial attention.

The measurement of emissions in the exhaust of a combustion source such as a diesel engine, a chimney, or a wood- or coal-burning stove generally requires conditioning of the sample before being amenable to real-time analysis for particulate content by existing analytic methods. The particles in the exhaust stream are typically very small in size (often referred to as "Ultrafine Particulate Matter") and have a high affinity for coagulating by accumulation into a smaller number of slightly larger particles. This tends to confound the analysis by optical single particle counters, or devices based upon measuring the reflection or scattering of light from the particles, since the reflection and scattering of light is a very strong function of the particle size. Coagulation of ultrafine particles into small particles confounds measurement methods based upon optical scattering or size determination. The exhaust stream also typically contains a high content of water vapor, derived from the combustion of the hydrogen in the hydrocarbon fuel to form water. This humidity will moisten any collection substrate and usually thereby contribute a substantial error to subsequent analysis. Finally, the exhaust stream is usually hot, potentially causing problems for an analytical instrument if the stream is passing through the instrument continuously.

For these reasons, conventional real-time analytical techniques for the study of the particulate content of direct combustion exhaust streams almost always dilute the exhaust sample continuously with a large excess of filtered, particle-free, dry injection air at room temperature. Dilution air is usually added in a ratio from 10:1 to 100:1 relative to the exhaust sample. Dilution separates the ultrafine particles, reducing coagulation of the particles. Dilution also reduces the net relative humidity, reducing errors when analyzed by collection-based techniques. Dilution further reduces the temperature from hot exhaust to close to room temperature, making it more suited to analysis by optical or electronic components.

The use of dilution also represents a substantial need for additional equipment such as pumps, flow controllers, valves and a mixing chamber; supported, in turn, by supplies of dry compressed air and other incidentals. Thus dilution-based real-time analysis of exhaust particulates is neither portable nor convenient to use for measuring emissions at their source.

There is a need for apparatus and methods that allow for obtaining a rapid sample of the direct, undiluted exhaust emissions stream and performing an instantaneous analysis for black carbon content using analytical techniques. Such an apparatus and method should be easy to use and inexpensive, and not require the use of specialty diluent gas or excessive pumps, valves, and components for diluting a sample. The apparatus should be portable, should not require supporting infrastructure such as the provision of dry compressed air; and should be able to collect and analyze a sample in a short time, such as less than 30 seconds.

BRIEF SUMMARY OF THE INVENTION

The present invention overcomes the disadvantages of prior art by, in one embodiment, providing a method of analyzing particles collected on a filter from a predetermined or measured volume of sample gas. The method includes providing a first flow of background gas to the filter, where the first flow of background gas is sufficient to allow the filter to reach equilibrium values of temperature and moisture with the background gas. The method further includes performing a first analytical measurement on the filter, then flowing the predetermined or measured volume of sample gas through the filter, and thereafter providing a second flow of background gas to the filter, where the second flow is sufficient to allow the filter to reach equilibrium values of temperature and moisture with the background gas. The method still further includes performing a second analytical measurement on the filter after the flowing of the sample gas through the filter; and determining a measurement of particles in the sample gas from the first analytical measurement and the second analytical measurement.

The sample gas may be an exhaust gas. The background gas may be an ambient gas, a bottled gas, or a gas is filtered to remove any particulates in the background gas.

In one embodiment, the predetermined or measured volume is a predetermined volume, and where the flowing the sample gas includes obtaining a predetermined flow rate of gas for a predetermined time. In another embodiment, the predetermined or measured volume is a measured volume, and where the flowing the sample gas includes measuring the volume of sample gas.

In yet another embodiment, the volume of sample gas is less than 10 milliliters, and the volume of sample gas is obtained in less than 5 seconds.

In certain embodiments, the equilibrium values of temperature and moisture of the filter after the first flow of background gas is approximately the same as the equilibrium values after the second flow of background gas.

In another embodiment, a method of analyzing particles in a predetermined or measured volume of sample gas provided to an apparatus. The method includes purging the apparatus with a first flow background gas, where the apparatus includes a gas inlet, a filter configured to collect particles in a gas provided to the inlet, and an analyzer for measuring properties of the particles collected on the filter, where the purging is sufficient for the temperature of the filter and moisture on the filter to reach equilibrium values of filter temperature and moisture with the background gas. The method further includes performing a first analytical measurement on the filter after providing the first flow of background gas, and flowing the predetermined or measured volume of sample gas through the inlet, and then providing a second flow of background gas through the inlet, where the second flow is sufficient to displace the volume of sample gas to the filter and the filter to reach equilibrium values of filter temperature and moisture with the background gas. The method further includes performing a second analytical measurement on the filter after providing the second flow of background gas; and determining a measurement of particles in the sample gas from the first analytical measurement and the second analytical measurement.

Yet other embodiments provide an apparatus for batch analyzing a volume of sample gas for particles. The apparatus includes a probe adapted to accept the sample gas and a background gas; a gas holding volume to accept gas from the probe; an analyzer to accept gas from the gas holding volume, where the analyzer includes a filter to collect particles from the gas and perform measurements on the filter; a flow system to provide air flow from the probe to the filter; and electronics programmed to operate the apparatus to perform a method. The method includes providing a first flow of background gas to the filter, where the first flow of background gas is sufficient to allow the filter to reach equilibrium values of temperature and moisture with the background gas; performing a first analytical measurement on the filter; flowing the predetermined or measured volume of sample gas through the filter, and thereafter providing a second flow of background gas to the filter, where the second flow is sufficient to allow the filter to reach equilibrium values of temperature and moisture with the background gas; performing a second analytical measurement on the filter after the flowing of the sample gas through the filter; and determining a measurement of particles in the sample gas from the first analytical measurement and the second analytical measurement.

Many of the features together with the various ancillary provisions will become apparent to those skilled in the art from the following detailed description, which are attained by the sample collecting apparatus and method of the present invention, certain embodiments thereof being shown with reference to the accompanying drawings, by way of example only, wherein:

Reference symbols are used in the Figures to indicate certain components, aspects or features shown therein, with reference symbols common to more than one Figure indicating like components, aspects or features shown therein.

DETAILED DESCRIPTION OF THE INVENTION

Figure 1:
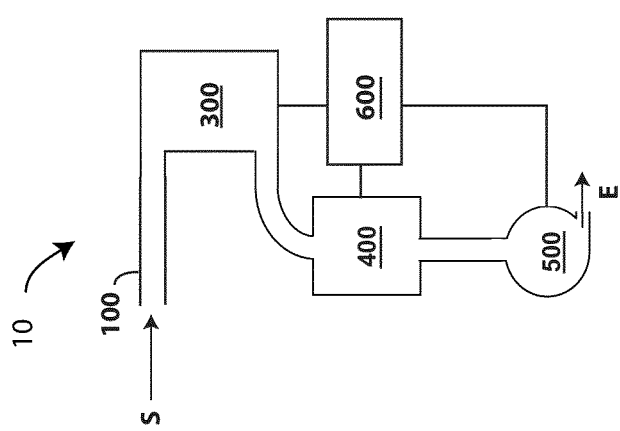
FIG. 1 is a schematic of a first embodiment of an apparatus for measuring black carbon particles.

FIG. 1 is a schematic illustration of one embodiment of an apparatus 10 for measuring black carbon particles. Apparatus 10 includes: a probe 100; an analyzer 300; an air flow sensor 400; a vacuum pump 500; and electronics 600. Probe 100, analyzer 300, air flow sensor 400, and vacuum pump 500 form a conduit for the flow of a fluid. Thus, for example, FIG. 1 shows a sample S which enters probe 100, continues into analyzer 300, and exits vacuum pump 500 as a flow E.

In general, the flow of a gas is controlled by the operation of vacuum pump 500 which draws gas into apparatus 10 sequentially through probe 100, analyzer 300, where particulate measurements are made, and air flow sensor 400, where the sample flow rate is determined. Electronics 600, which may instruct the user on where or how to place probe 100, receives an indication of the flow rate from air flow sensor 400, operates vacuum pump 500 to draw a predetermined quantity gases through probe 100, and collects data from analyzer 300.

As discussed subsequently, apparatus 10 may be operated in a "batch mode" for determining the properties of a particle-laden gas. In addition, the gas provided to apparatus 10 may vary over time. Thus, for example and without limitation, apparatus 10 may be operated so that sample S alternates between a first gas, which may be an exhaust stream containing particles, and a second, background gas, which may be ambient air, filtered ambient air, or a bottled gas, where the flow of the second gas flushes the first sample of exhaust gas through analyzer 300.

Analyzer 300 measures a property of sample S. Embodiments of the present invention may be used with a wide variety of analyzers known in the art. In one embodiment, analyzer 300 collects particles in sample S on a filter (not shown in FIG. 1) and performs an optical measurement to determine an amount of particles. One class of such analyzers is known as differential photometric analyzers, wherein the differences between sequential optical measurements are used to estimate particulate concentrations. Thus, for example and without limitation, analyzer 300 may be an AETHALOMETER® (Magee Scientific Company, Berkeley Calif.) (see for example, U.S. Pat. No. 4,893,934 and U.S. Pat. Pub. No. 2010-0027013, the contents of which are incorporated herein by reference, and the paper entitled "The Aethalometer—An Instrument for Real-Time Measurement of Optical Absorption by Aerosol Particles," Hansen, A. D. A., Rosen, H., and Novakov, T., *The Science of the Total Environment* 36 (1984) 191-196). Alternatively, analyzer 300 may be another type of differential photometric analyzer known as a Multi Angle Absorption Photometer (see, for example, U.S. Pat. No. 7,038,765, the contents of which are incorporated herein by reference), or the Particle Soot Absorption Photometer (see, for example, Bond, T. C., Anderson, T. L., Campbell, D., "Calibration and intercomparison of filter-based measurements of visible light absorption by aerosols," Aerosol Science and Technology, vol. 30, pp 582-600, 1999).

Analyzer 300 may also be, for example and without limitation, an apparatus that detects electrons transmitted through a filter having collected particles, as in instruments such as the Beta Attenuation Mass Monitor (see, for example, Macias, E. S.; Husar, R. B., "Atmospheric particulate mass measurement with beta attenuation mass monitor," Environmental Science and Technology, vol. 10, September 1976, p. 904-907); measurements of the vibrational frequency of the filter, as in instruments such as the Tapered Element Oscillating Microbalance (see, for example, Patashnick, H.; Rupprecht, G. "The tapered element oscillating microbalance: A monitor for short-term measurement of fine aerosol mass concentration," Final Report, October 1977-December. Dudley Observatory, Albany, N.Y., 1980.); changes in the electrical properties, as in instruments such as electrochemical gas analyzers; measurements of radiation from radioactive particulates; or measurements of magnetic properties in the filter.

Air flow sensor 400 measures the flow of sample air drawn through the system. Air flow sensor 400 preferably responds quickly to changes in air flow, and may be, for example and without limitation, an air mass flow sensor.

Vacuum pump 500 draws the sample air through air flow sensor 400 and analyzer 300. Pump 500 preferably can be started and stopped very quickly. Vacuum pump 500 may be, for example and without limitation, a miniature rotary vane pump.

Electronics 600 is in communication, through wired and/or wireless connections, with analyzer 300, air flow sensor 400, and vacuum pump 500. Electronics 600 may this, for example and without limitation, include analogue and/or digital components, including but not limited to a programmable digital computer, to control vacuum pump 500, to determine the flow rate as measured by air flow sensor 400, and to obtain a measurement from analyzer 300. Electronics 600 may also include means such as display to instruct the user on where or how to place probe 100, and provide signals or indications to the user regarding operation and/or readings from analyzer 300.

In certain embodiments, vacuum pump 500 is operated to maintain a predetermined flow rate. Thus, for example, the output of air flow sensor 400 corresponding to a predetermined flow rate is stored in electronics 600. Electronics 600 utilizes feedback control from sensor 400 and the predetermined flow rate to provide a signal to a motor of vacuum pump 500 to achieve the predetermined flow rate. In certain other embodiments, electronics 600 operate pump 500 for some predetermined time. In certain other embodiments, one or more of the predetermined flow rate and/or predetermined time may be varied so suit particular conditions. Thus, for example, if a sample has a low particle concentration, it may be desirable to collect more particulates by operating pump 500 at a higher rate and/or for a longer time.

Figure 2:
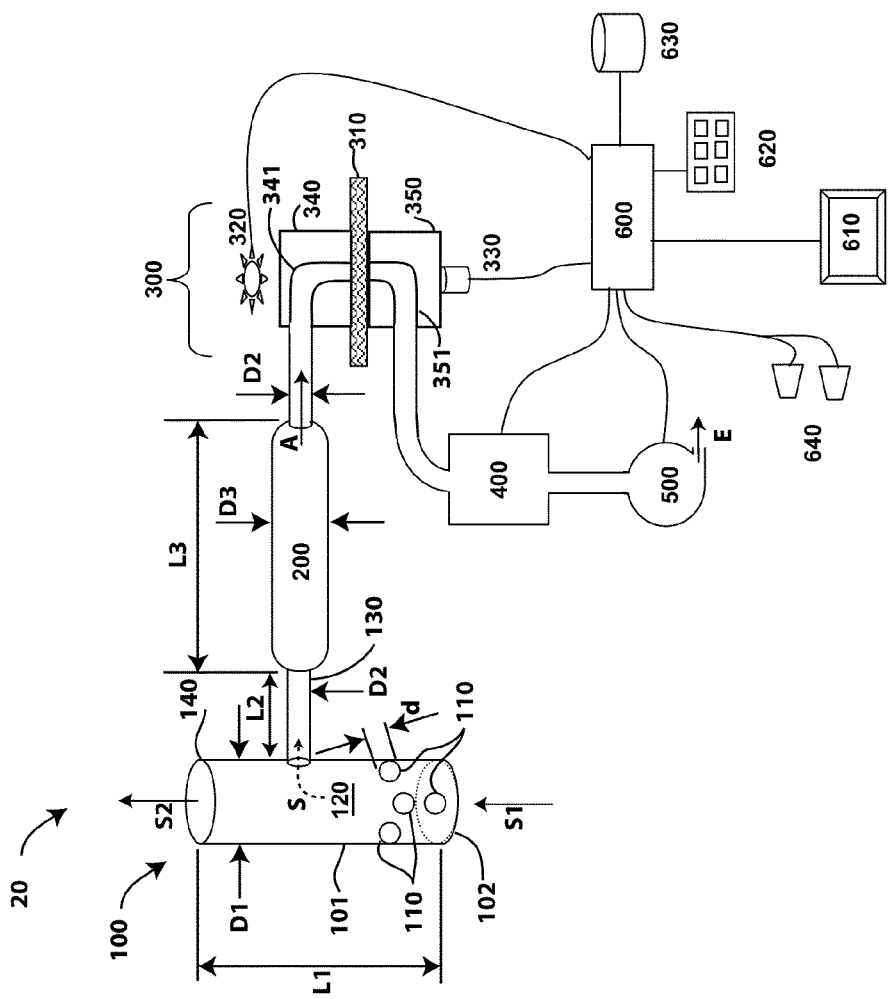
FIG. 2 is a schematic of a second embodiment of an apparatus for measuring black carbon particles.

FIG. 2 is a schematic illustration of a second embodiment of an apparatus 20 for measuring black carbon particles. Apparatus 20, which includes a volume 200 that provides a flow passage that connects probe 100 and analyzer 300, is generally similar to apparatus 10, except as explicitly stated.

Probe 100 is configured to allow create a stagnation region from which collect a sample from a flow. Probe 100 of apparatus 20 is includes a tube 101 having several entrance perforations 110, an otherwise closed end 102 with one perforation 110, an internal flow zone 120, a branching sample extraction port 130, and a tube exit 140.

The tube is placed in a flow S1, a portion of the flow enters port 130 as flow S, and the remainder of the flow exits as flow S2 through exit 140. A probe 100 thus configured may be inserted into a rapidly-flowing exhaust stream such as an engine tailpipe and may extract a sample of exhaust gases without the effects of positive or negative pressure that might be created by rapid flow either passing by or impinging on a directly-inserted sample extraction tube.

In one illustrative embodiment, tube 101 is formed stainless steel tube having a diameter D1 of 0.5 inches and a length L1 of 1 inch. Perforations 110 have a diameter of $\frac{1}{16}$ inch, and extraction port 130 has an inner diameter D2 of $\frac{1}{8}$ inch and may extend a length L2 of several inches.

Volume 200 may be formed, for example and without limitation, from tubing that connects probe 100 to analyzer 300. Volume 200 of FIG. 2 is shown as having an enlarged cross-sectional area, and provides a region where the gas may be accumulated or mixed. In one illustrative embodiment, volume 200 has a diameter D2 of $\frac{3}{8}$ inch and a length L3 of 4 inches.

Analyzer 300 as shown in FIG. 2 may be operated as a differential photometric analyzer known as an AETHALOMETER® (Magee Scientific Company, Berkeley Calif.) (see for example, U.S. Pat. No. 4,893,934, U.S. Pat. Pub. No. 2010-0027013, and U.S. Provisional Application No. 61/322, 060, the contents of which are incorporated herein by reference, and the paper entitled "The Aethalometer—An Instrument for Real-Time Measurement of Optical Absorption by Aerosol Particles," Hansen, A. D. A., Rosen, H., and Novakov, T., *The Science of the Total Environment* 36 (1984) 191-196).

Analyzer 300 provides a flow passage having a diameter of $\frac{1}{8}$ inch and includes a fibrous filter 310, a light source 320, a light detector 330, and light-transmitting inlet assembly 340 and outlet assembly 350 having passageways 341 and 351, respectively. Filter 310 may be, for example and without limitation, a replaceable quartz fiber filter tape that is intended for performing optical transmission measurements for the determination of the presence of particulates. Assemblies 340 and 350 control the flow of air while simultaneously allowing the passage of light for obtaining optical measurements on filter 310.

Filter 310 is sandwiched between assemblies 340 and 350 with passageways 341 and 351 aligned on each side of filter 310, with passageway 341 configured to accept gas from volume 200 and passageway 351 configured to provide gas to sensor 400. Fibrous filter 310 collects particles from the air stream passing through it. Light source 320 illuminates the upper surface of filter 310, and light detector 330 measures the intensity of light transmitted through the filter. The intensity of light from source 320 is reduced by the accumulation of black particles, as measured by light detector 330.

Analyzer 300 thus samples particles suspended in an air stream and collects them by the continuous filtration of a porous, fibrous substrate, and then measures the transmission of light through the filter. The optical transmission is, in general, affected by the amount of black carbon particles collected.

In one embodiment, analyzer 300 provides the flow onto an area on filter 310 of 0.71 $cm^2$, can sense changes in the optical density of from 0.05 to 2.0 Optical Density Units, which corresponds to black carbon loading of 0.4 to 16 micrograms/ $cm^2$ of filter area. For conditions where the flow rate and times for exhaust sampling are within this range, the optical density, filter area, and sample collection volume of apparatus 20 may be combined to give a black carbon loading in, for example, micrograms per volume of exhaust.

In one embodiment, sensor 400 is an Omron model D6F MEMS Flow Sensor (Omron Corporation, Kyoto, Japan), which provides a voltage proportional to the mass flow through the sensor. In certain embodiments, the flow rates measured is on the order of 50 to 100 milliliters per minute.

In certain embodiments, pump 500 is capable of drawing up to 1 liter per minute of gas, and the speed of the pump is controlled by a voltage provided to the pump motor.

In general, electronics 600 may include a controller for pump 500, the ability to obtain a reading from sensor 400 and from analyzer 300, and programming to control the timing and operation of the pump and analyzer and, in some embodiments, to provide signals or indications to the user regarding operation and/or readings from the analyzer. In another embodiment, electronics 600 includes a connector for connecting to a computer for controlling and/or obtaining data from the analyzer.

In one embodiment, electronics 600 may include: circuits and/or programming to acquire and process the signals provided by the optical detector 330 and the air flow sensor 400; to control the operation of the pump 500; and to process these signals according to a program whose purpose is to control the functioning of the device, acquire certain data, and calculate the desired end result. Electronics 600 may or may not be associated with a display screen 610 or other device providing direct information to the user; a keypad, touch-sensitive device or other input device 620 allowing the user to enter information or specify operational parameters; a data storage device 630 allowing both the operational parameters, test identification and test results to be recorded; functional switch(es) 640 allowing the user to signal completion of certain required actions; and other data input and output devices. Alternately, these functions may be performed by a portable computing device 640 connected either wirelessly or by wire to the sampling and analytical device.

Figure 3:
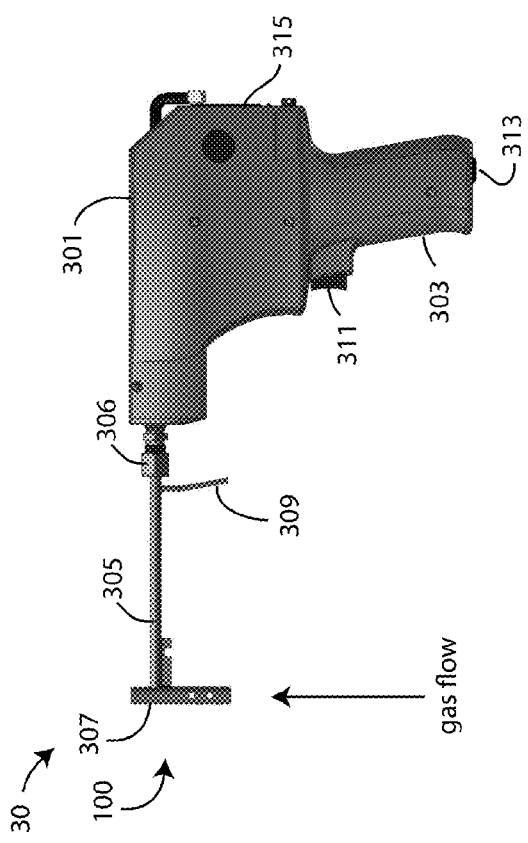
FIG. 3 is a drawing of a first embodiment of an apparatus for measuring black carbon particles.
Figure 4:
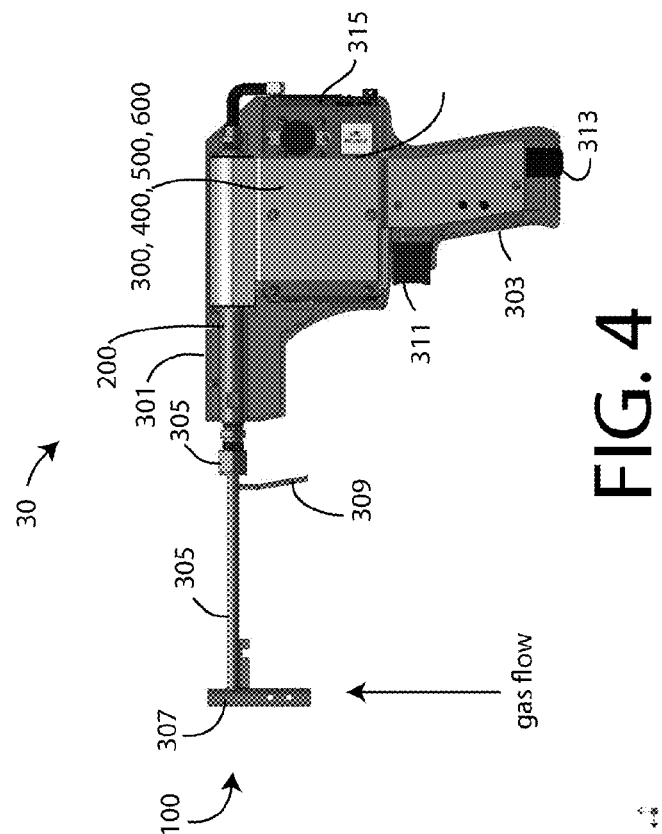
FIG. 4 is a sectional drawing of the embodiment of FIG. 3.

FIG. 3 is a drawing of a first embodiment of an apparatus 30 for measuring black carbon particles, and FIG. 4 is a sectional drawing of the embodiment of FIG. 3. Many of the components discussed in FIGS. 1 and 2 are shown in FIGS. 3 and 4. Specifically, apparatus 30 may include one or more elements of apparatus 10 or 20.

As shown in FIGS. 3 and 4, a black carbon measuring apparatus 30 includes a housing 301 with a grip 303 and a probe extension 305, including a rotatable joint 306, that supports a probe 307, which may be, for example and without limitation, probe 100. Probe extension 305 has a protruding alignment rod 309 and also rotates about its axis. Alignment rod 309 may thus allow probe 307 to be aligned from the air flow separately from housing 301. Housing 301 also includes a filter receptor 315 for inserting and/or removing filters, such as filter 310.

Housing 301 has a trigger 311, which may act as an input device to apparatus 30, a cord connector 313 for connecting to a separate computer system, such as electronics 600, which may contain some or all of the programming or instructions for operating apparatus 30, or may provide means for downloading information from the apparatus. Alternatively, apparatus 30 may have a wireless adaptor for computer connectivity.

Interior to housing 301 is analyzer 300, which may include, for example and without limitation, the volume 200, analyzer 300, flow sensor 400, pump 500, and electronics 600 of apparatus 10, and probe extension 305 is volume 200. By way of example, and without limitation, apparatus 30 is apparatus 20, trigger 311 is switch 640, and a separate computer (not shown) may be connected to the apparatus 30 via a cord connector 313.

Principle of Operation:

In certain embodiments, apparatus 10, 20, or 30 is operated to perform measurements on a sample of a combustion exhaust stream by the following steps: 1) drawing in a volume of background air to equilibrate the temperature and moisture content of the filter; 2) performing a first analytical measurement on the filter; 3) drawing in a known (or determined) volume of exhaust gas; 4) drawing in a second volume of background air sufficient amount to flush substantially all of the exhaust gas through the filter and to return the filter to the same temperature and moisture content as in step 1; and 5) performing a second analytical measurement on the filter. The background air may be ambient air, ambient air filtered to remove particulates, or bottled air.

This method essentially analyzes the entirety of the sample to measure its black carbon content by optical analysis. If the ambient air contains, by comparison, virtually no black carbon particulates, the measurement is of the particulates in a known (or determined) volume of exhaust, and is independent of the amount of admixed ambient air. If the ambient air does contain particles, then the ambient air may or may not be filtered prior to use in the apparatus. The particle concentration may be determined by dividing the total amount of particles collected from the exhaust by the volume of exhaust collected.

The volume of particle-laden gas is determined by the particle concentration and the analyzer sensitivity. The volume may be, for example and without limitation, greater than 100 milliliters, between 1 milliliter and 100 milliliter, less than approximately 100 milliliters, less than approximately 10 milliliters, less than approximately 5 milliliters, or less than approximately 1 milliliters. The sample may be obtained in less than approximately 1 minute, less than approximately 30 seconds, less than approximately 10 seconds, less than approximately 5 seconds, or less than approximately 1 second.

One example of the operation of apparatus 10, 20, or 30, where analyzer 300 is an AETHALOMETER®, is as follows:
A. Analyzer 300 is Prepared for Use
  a. Analyzer 300 is turned on and pump 500 is turned off (zero flow rate)
  b. A clean filter 310 is inserted into analyzer 300
  c. Probe 100 is placed in clean air
B. Initial Measurement
  d. Pump 500 is operated an air flow rate of F1 for T1 seconds and then turned off
  e. Analyzer 300 measures an initial filter 310 optical transmission, having value ATN1
C. Collect Sample
  f. Probe 100 is placed in exhaust stream
  g. Pump 500 is operated at an air flow rate of F2 for T2 seconds and then turned off
D. Final Measurement
  h. Probe 100 is placed in clean air
  i. Pump 500 is operated at an air flow rate of F3 for T3 seconds and then turned off
  j. Analyzer 300 measures the final filter 310 optical transmission, having value ATN2
E. Calculation
  k. Electronics 600 calculates [BC] in exhaust stream from ATN1, ATN2, T2 and F2.

In an alternative embodiment, apparatus 10, 20, or 30 includes additional programming or steps executed by electronics 600 to automate some or all of the steps for obtaining a black carbon measurement. As an example of such an embodiment, the following may be prompted by electronics 600:

Steps 1-3 prepare apparatus 10, 20, or 30 for use (Step A, above):

1. Electronics 600 prompt the user to enter identifying information for electronic storage. The identifying information may include but is not limited to, describing the nature of the source, the test, the conditions, and any other pertinent information.
2. Electronics 600 prompt the user to provide a file name under which the data will be stored electronically.
3. Electronics 600 prompt the user to insert a fresh, clean filter 310 into analyzer 300.

Steps 4-6 fill are an initial measurement, where volume 200 is provided with a fresh, relatively particle-free gas and provide a background reading of this gas in analyzer 300 (Step B, above):

4. Electronics 600 prompt the user to position probe 100 in ambient air, well-separated from the direct combustion exhaust stream or smoke plume which is to be measured.
5. Upon confirmation by the user that probe 100 is in ambient air, electronics 600 activate pump 500 for a time T1 seconds at an air flow rate of F1 liters per minute as measured by the air flow sensor 400. This permits the fibers of the filter material 310 to become equilibrated with the ambient air conditions of temperature, relative humidity, and any other parameters that may affect the optical transmission of the filter, and also fills the inlet volume 200 with air of local ambient temperature and pressure.
6. Upon completion of the previous step, electronics 600 activate light source 320 to illuminate the filter spot and acquire an optical signal from light detector 330 to perform a measurement of the optical transmission of the filter before collection of the sample. This optical transmission is converted to an absorbance or Optical Attenuation value designated ATN1.
7. At the end of the time T1, electronics 600 turn off pump 500, so the air flow reverts to zero.

Steps 8 and 9 are the sample collection steps, wherein a predetermined, or measured, amount of exhaust gas into volume 200 (Step C, above):

8. Electronics 600 prompt the user to insert sampling probe 100 into the exhaust stream under study.
9. Upon confirmation by the user that probe 100 is positioned in the exhaust stream, electronics 600 activate pump 500 for a time T2 seconds at an air flow rate of F2 liters per minute as measured by the air flow sensor 400. This draws in a quantity of the exhaust sample into volume 200 which had previously been filled with air of local ambient temperature and humidity.

Steps 10-12 are the final measurement steps, wherein ambient air is drawn into apparatus 20, to push the exhaust gas through analyzer 300 (Step D, above):

10. At the end of the time T2, electronics 600 turn off pump 500, prompting the user to withdraw probe 100 from the exhaust stream and prompting the user to place the probe in ambient air.
11. Upon confirmation by the user that probe 100 is in ambient air, electronics 600 activate pump 500 for a time T3 seconds at an air flow rate of F3 liters per minute as measured by the air flow sensor 400.
12. At the end of time T3, electronics 600 turn off pump 500, activate light source 320 to illuminate the filter spot, and acquire a signal from the light detector 330 to perform a measurement of the optical transmission of the filter after collection of the sample. This optical transmission is converted to an absorbance or Optical Attenuation value designated ATN2.

In step 13, the calculation of particulate concentration is performed (Step E, above)

13. Electronics 600 performs calculations, data display and storage functions.

Typical operating conditions of apparatus 10, 20, or 30 may include the following sampling parameters, which are useful for diesel exhaust:

Pre-sampling equilibration (the initial sampling of ambient air) is performed for T1=5 to 10 seconds at an air flow rate of F1=50 to 100 milliliters per minute:

Sample collection is performed for T2=5 seconds at an air flow rate of F2=50 milliliters per minute;

Post-sampling equilibration (the second sampling of ambient air) is performed for T3=10 to 20 seconds at an air flow rate of F3=50 to 100 milliliters per minute.

Thus, the total volume of hot, moist, concentrated exhaust that is withdrawn is on the order of a few milliliters in total. This gas is easily diluted in volume 200 of some tens of milliliters. The totality of this sample-containing volume is then drawn through the spot on filter 310 by the post-sampling equilibration flow. Using these conditions, black carbon concentrations in diesel exhaust have been measured in the range of from 0.1 to 100 milligrams/m$^3$.

Steps (6), (9), (11), and (12) above act to cool and dehumidify introduce the hot, moist and concentrated exhaust sample collected by probe 100. The above steps also sweep out the diluted sample onto the filter 310, and the subsequently draws ambient air through the fibers of the filter material, removing any excess moisture or temperature to ambient levels, and re-equilibrating the filter to conditions identical to that with which it was initially equilibrated under step (5). The difference, however, is that the totality of the black carbon particles that were aspirated into the inlet during step (9) have now been swept onto the filter 310, creating a spot of greater darkness.

When a small volume of exhaust sample is aspirated into volume 200, it becomes cooler, less concentrated and drier. However, the degree of this conditioning is immaterial, because in the subsequent post-sampling equilibration flow (step 11), the totality of the collected sample material is swept through the filter 310 and retained for analysis. The analysis is based upon total mass of black carbon material and is insensitive to the size or shape of the individual particles: only their total mass is to be determined. The post-sampling equilibration step (11) performs two functions: it sweeps the totality of the sample through the filter, and it reconditions the filter fibers to the initial ambient levels of temperature and moisture content. This ensures that the differences between ATN2 and ATN1 (step (12) minus step (6)) are due only to the intervening accumulation of black carbon particles on the filter, and are not influenced by changes in temperature or moisture content of the filter fibers. In particular, as long as step (11) draws all of the particles collected in step (9) onto filter 310, the measurement will not be greatly affected by the amount of admixed flushing air.

The difference in optical absorption of the spot between the pre-sampling and post-sampling measurements is ATN2−ATN1 and is a direct indicator of the density of optically-absorbing black carbon material collected on the filter spot from the small volume of sample air collected during step (9). This amount of black carbon is calculated in units of mass, usually micrograms or nanograms. This mass of material is then divided by the air volume of the sample in cubic meters collected during step (9), namely the flow rate F2 multiplied by the sample duration T2. The result is the average concentration of black carbon in the sample stream, expressed in conventional units of grams per cubic meter. This result is then displayed to the user and stored to the data file together with the accompanying descriptive information that had been input in step (1).

In one embodiment, the black carbon concentration is calculated as follows. The attenuation (ATN1 and ATN2) is proportional to the logarithm of the intensity of light (S1 and S2) measured through the filter, for example as $ATN1=100 \ln(S0/S1)$, where S0 is a reference or background reading. The density of particles (mass per area of filter) is proportional to (ATN2−ATN1), i.e. increase in "blackness." The total amount of material (M, units of mass) is given by the density time the area of filter spot, such as by $M=(ATN2-ATN1)*A*C$, where A is the spot size (area) and C is a system calibration constant. The total exhaust flow (V) through the filter is given by the flow rate times the sample time duration, or $V=F2*T2$. Alternatively, the total exhaust flow volume is determined by integrating the output of airflow sensor 400. The concentration of material in exhaust stream is thus given as the amount of material/total exhaust flow volume, or $[BC]=M/V$, with units of mass per volume of air.

Another feature of this method is that since the measurements are taken after flowing a volume of ambient air through the filter, measurements are taken with the filter at the same temperature and moisture content. This may be important for filters whose optical properties vary with temperature and/or moisture content.

In certain embodiments, the predetermined flow rate and/or sampling time is varied to meet the particulate concentration of the exhaust. Thus, for example, automobile exhaust may contain an order of magnitude less particulate matter than diesel exhaust. The sample of automobile exhaust may be increased by increasing the predetermined flow rate and/or predetermined sampling time. In one embodiment, T2 is increased to 20 seconds and F2 increased to 100 ml/min, to collect an exhaust sample of 8 times larger volume than is collected for T2=5 seconds and F2=50 ml/min.

Since the optical analysis is essentially instantaneous, the entire cycle of equilibration, sampling, equilibration and measurement can be completed in half a minute to one minute. The result obtained represents a "snapshot" value of the black carbon concentration in the air stream at the instant of sampling.

It is an additional attribute of this system that the filter spot retains the totality of black carbon collected from the sample stream during the short duration of sample aspiration. Black carbon is extremely stable and non-volatile. Once collected on a filter, it will remain unchanged for many years. Some research samples have been re-analyzed at intervals of decades and are found to not lose any optical absorption. Thus, the sample collected on the spot of the filter 310 constitutes a permanent and visible record of the emissions. Dense emissions will create a dark spot that is readily visible. Light emissions, collected under the same parameters of flow rate and time, will create a proportionally lighter spot. In addition to providing evidence visible to the eye, the collected sample may also be subjected to other subsequent chemical or physical analyses, for example for specific toxic compounds, or specific heavy metals. The analysis for black carbon by measurement of optical transmission is non-destructive, non-contact, and non-contaminating. The sample represented by the spot on the filter may provide other information if subjected to other analyses.

Reference throughout this specification to "one embodiment," "an embodiment," or "certain embodiments" means that a particular feature, structure or characteristic described in connection with the embodiment is included in at least one embodiment of the present invention. Thus, appearances of the phrases "in one embodiment," "in an embodiment," or "in certain embodiments" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment.

Thus, while there has been described what is believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

I claim:

1. A method of analyzing particles collected on a filter from a predetermined or measured volume of sample gas, said method comprising:
    providing a first flow of background gas to the filter, where said first flow of background gas is sufficient to allow the filter to reach equilibrium values of temperature and moisture with the background gas;
    performing a first analytical measurement on the filter;
    flowing the predetermined or measured volume of sample gas through the filter, and thereafter providing a second flow of background gas to the filter, where said second flow is sufficient to allow the filter to reach equilibrium values of temperature and moisture with the background gas;
    performing a second analytical measurement on the filter after the flowing of the sample gas through the filter; and
    determining a measurement of particles in the sample gas from the first analytical measurement and the second analytical measurement,
    where the first analytical measurement and the second analytical measurement are performed by a differential photometric analyzer.

2. The method of claim 1, where said sample gas is an exhaust gas.

3. The method of claim 1, where said background gas is an ambient gas.

4. The method of claim 1, where said background gas is a bottled gas.

5. The method of claim 1, where said background gas is filtered to remove any particulates in the background gas.

6. The method of claim 1, where the predetermined or measured volume is a predetermined volume, and where said flowing the sample gas includes obtaining a predetermined flow rate of gas for a predetermined time.

7. The method of claim 1, where the predetermined or measured volume is a measured volume, and where said flowing the sample gas includes measuring the volume of sample gas.

8. The method of claim 1, where the volume of sample gas is less than 10 milliliters.

9. The method of claim 1, where the volume of sample gas is obtained in less than 5 seconds.

10. The method of claim 1, where the equilibrium values of temperature and moisture of the filter after the first flow of background gas is approximately the same as the equilibrium values after the second flow of background gas.

11. A method of analyzing particles in a predetermined or measured volume of sample gas provided to an apparatus, said method comprising:
   purging the apparatus with a first flow background gas, where the apparatus includes a gas inlet, a filter configured to collect particles in a gas provided to the inlet, and an analyzer for measuring properties of the particles collected on the filter, where the purging is sufficient for the temperature of the filter and moisture on the filter to reach equilibrium values of temperature and moisture with the background gas;
   performing a first analytical measurement on the filter after providing the first flow of background gas;
   flowing the predetermined or measured volume of sample gas through the inlet, and then providing a second flow of background gas through the inlet, where the second flow is sufficient to displace the volume of sample gas through the filter and have the filter to reach equilibrium values of temperature and moisture with the background gas,
   performing a second analytical measurement on the filter after providing the second flow of background gas; and
   determining a measurement of particles in the sample gas from the first analytical measurement and the second analytical measurement.

12. The method of claim 11, where said sample gas is an exhaust gas.

13. The method of claim 11, where said background gas is an ambient gas.

14. The method of claim 11, where said background gas is a bottled gas.

15. The method of claim 11, where said background gas is filtered to remove any particulates in the background gas.

16. The method of claim 11, where said flowing of the predetermined or measured volume of sample gas includes flowing the sample gas into the apparatus for a predetermined time at a predetermined flow rate.

17. The method of claim 11, where said flowing of the predetermined or measured volume of sample gas includes measuring the volume of the sample gas.

18. The method of claim 11, where the volume of sample gas is less than 10 milliliters.

19. The method of claim 11, where the volume of sample gas is obtained in less than 5 seconds.

20. The method of claim 11, where the analyzer is a differential photometric analyzer.

21. The method of claim 11, where the equilibrium values of temperature and moisture of the filter after the first flow of background gas is approximately the same as the equilibrium values after the second flow of background gas.

22. An apparatus for batch analyzing a volume of sample gas for particles, said apparatus comprising:
   a probe adapted to accept the sample gas and a background gas;
   a gas holding volume to accept gas from the probe;
   an analyzer to accept gas from the gas holding volume, where the analyzer includes a filter to collect particles from the gas and perform measurements on the filter;
   a flow system to provide air flow from the probe to the filter; and
   electronics programmed to operate the apparatus to perform the method of:
      providing a first flow of background gas to the filter, where said first flow of background gas is sufficient to allow the filter to reach equilibrium values of temperature and moisture with the background gas;
      performing a first analytical measurement on the filter;
      flowing the predetermined or measured volume of sample gas through the filter, and thereafter providing a second flow of background gas to the filter, where said second flow is sufficient to allow the filter to reach equilibrium values of temperature and moisture with the background gas;
      performing a second analytical measurement on the filter after the flowing of the sample gas through the filter; and
      determining a measurement of particles in the sample gas from the first analytical measurement and the second analytical measurement.

23. The apparatus of claim 22, where said electronics are programmed to accept the sample gas for a predetermined time at a predetermined flow rate.

24. The apparatus of claim 22, where said electronics are programmed to measure the volume of the obtained sample gas.

25. The apparatus of claim 22, where said electronics are programmed to accept a volume of sample gas of less than 10 milliliters.

26. The apparatus of claim 22, where said electronics are programmed to accept a volume of sample gas in less than 5 seconds.

27. The apparatus of claim 22, where the analyzer is a differential photometric analyzer.

* * * * *